United States Patent [19]

McGredy, IV

[11] Plant 5,036

[45] Apr. 12, 1983

[54] HYBRID SHRUB ROSE CV. MACMIGMOU

[75] Inventor: Samuel McGredy, IV, Auckland, New Zealand

[73] Assignee: Armstrong Nurseries, Inc., Ontario, Calif.

[21] Appl. No.: 314,243

[22] Filed: Oct. 23, 1981

[51] Int. Cl.[3] ..... A01H 5/00

[52] U.S. Cl. ..... Plt./2

[58] Field of Search ..... Plt./1-2

*Primary Examiner*—Robert E. Bagwill

*Attorney, Agent, or Firm*—Synnestvedt & Lechner

[57] ABSTRACT

A pillar rose having blossoms with a distinctive white eye.

1 Drawing Figure

1

This invention relates to a new rose cultivar (Macmigmou) of the hybrid shrub type. The plant is a tall, bushy pillar outdoor seedling cultivated primarily for garden decoration.

The seed parent was "Anytime" and the pollen parent was "Eyepaint" (U.S. Plant Pat. No. 3,985). The descriptive and comparative references to this plant and its bloom will relate to plants of the same class grown in the Ontario, Calif. region. This variety preserves its distinguishing characteristics through succeeding propagations by grafting and by budding.

This new variety is most readily distinguished from its seed parent, Anytime, by the combination of the following characteristics. The new rose Macmigmou is classed as a hybrid shrub whereas Anytime is considered to be of the hybrid miniature class. Anytime bears flowers of a relatively uniform salmon orange coloration whereas the new rose Macmigmou bears flowers of bright orange and white as described hereinafter. The flowers of Anytime have an unusual lavender "eye" coloration whereas the flowers of the rose Macmigmou have a distinctive near white "eye" as described hereinafter. The rose Anytime bears flowers of ¾" to 1" in diameter and the flowers of the new rose Macmigmou are significantly larger—from 2" to 2½" in diameter.

The new variety differs from its pollen parent, Eyepaint, most notably in the following respects. Whereas Eyepaint bears flowers of red and white coloration, the new rose Macmigmou bears flowers of orange and white coloration as described and shown herein. Eyepaint bears flowers consisting of 5 or 6 petals; whereas the new rose hybrid bears flowers of 10 to 14 petals and (in Ontario, Calif.) is considerably more floriferous than its pollen parent.

Several flowers of the new rose Macmigmou are usually borne in irregular, pyramidal clusters on strong medium to long stems. The plant blooms very abundantly when grown outdoors and nearly continuously during the growing season. The blooms have a slightly musky fragrance.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based on The R.H.S. Colour Chart, put out by The Royal Horticultural Society in London.

2

BUD

The peduncle is short to average length, average caliper, erect, stiff and moderately smooth, with some stipitate glands. The color is between Yellow Green, 147A and 147B.

Before the calyx breaks, the bud is small in size, of moderately short ovoid to globular form with some stipitate glands on the surface of the bud. Usually, slender foliaceous parts extend beyond the tip of the bud one-half or more of its length.

As the calyx breaks, the color is between Red, 38C, and Red, 36C; sometimes blushed with Red near 47B. The inner surface of the sepals carries a fine wooly tomentum; margins are lined with stipitate glands and hairs.

As the first petal opens, the bud is small in size, and of short, pointed, ovoid to globular form. The color of the outside basal attachment zone is near Yellow, 8B and suffuses to near Yellow 8D. About ¼" from attachment point, the color deepens to near Red 38C and sometimes is blushed with coloration near Red 47D. The inside basal attachment zone is of the same coloration as on the outside of the petal and about ¼" from the attachment point the color abruptly changes to a coloration near Red 44A for the remainder of the petal. The bud opens up well, and is not retarded or prevented from opening by cold, hot, wet or dry weather.

BLOOM

The size of the bloom when fully open is small, being from 2" to 2½" in diameter. Petalage is semi-double, with from 10 to 14 petals, plus 1 to 5 petaloids arranged regularly. The bloom is flat at first, becoming open to cupped. At first the petals remain somewhat loosely cupped, becoming later at maturity more loosely cupped.

PETALS

The petals are medium to thick in texture, with a satiny inside and outside. The outside petals are broadly obovate, the apex having a single notch. Intermediate petals are obovate, the apex having a single notch. Inside petals are narrowly obovate and have a single notch at the apex. The colors may be modified by being bordered or margined or penciled or striped or dotted, or blotched or shaded and/or washed or tinted with other colors.

The paragraph immediately following describes color values observed in a flower newly opened in the month of May. The plant had been grown outdoors, in Ontario, Calif.

The outer surface of all petals (outside, intermediate and inner) at the basal attachment point is near Yellow, 8B suffusing to near Yellow, 8D; toward the petal edge color deepens to near Red 38C. The basal colorations of the inner surfaces of all petals (outside, intermediate and inner) were essentially the same as the outside petals, but about ¼" from the basal attachment point the color abruptly changes to between Red, 44A and Red, 42B for the remainder of the petal.

The following paragraph describes color values observed in a flower which had been open for three days in the month of May. The plant had been grown outdoors, in Ontario, Calif.

The coloration of the outer surface of both the outside petal and the inside petal was the same as for the newly opened flower described above. The inner surface of the outside petals exhibit, at the basal attachment point, a coloration of about Yellow, 8B suffusing to near Yellow, 8D; about ¼" from the basal attachment point the color changes abruptly to between Red 43B and Red, 48A for the remainder of the petal. The coloration of the inner surface of inside petals was the same as for the newly opened flower described above.

The general color effect of the newly opened flower is between Red, 44A and Red, 42B with a whitish "eye" near Yellow, 8D and bright stamens near Yellow Orange, 15A. The general color effect in a flower that had been three days open is between Red, 43B and Red 48A with a whitish "eye" near Yellow 8D and stamens near Greyed-Orange, 165A. The aged flower falls off cleanly. It is not particularly affected by cold, hot, wet or dry weather.

The flower on the bush in the garden persists for from 3 to 4 days in the month of May.

REPRODUCTIVE ORGANS

Many stamens are arranged regularly about pistils.

The filaments are medium-length, and most are with anthers.

The anthers are small to medium in size, all opening at about the same time. The color when immature is near Yellow, 13A and near Greyed-Orange, 165B when mature.

There is a moderate amount of pollen which is near Yellow, 13C in color.

The pistils are approximately 30 in number, this being average.

The styles are moderately uneven, short to average length, of thin caliper, and somewhat bunched.

The stigma is near Yellow, 8B in color.

The ovaries are usually all enclosed in the calyx.

The hips are of average length, globular, with an inconspicuous neck and are of a coloration near Orange-Red, 33B; they are moderately smooth with thick, fleshy walls.

The sepals are of medium length, spear-shaped and recurved; their color on the inside is near Green, 138A and near Yellow-Green, 144B on the outside.

Seeds of small to medium size occur in average number (i.e., 8 to 15).

FOLIAGE

The compound leaves usually comprise 3 to 7 leaflets. They are abundant, of medium size, heavy to somewhat leathery and semi-glossy. The leaflets are ovoid, with apex acute, base round and margin simply serrate.

The upper surface of the mature foliage is between Green, 139A, and Yellow-Green, 147A, in color. The under surface is near Green 138A.

The upper surface of young foliage is between Green, 139A and Yellow-Green 147A and is suffused heavily with near Greyed-Purple 187B. The under surface is near Green 138B suffused heavily with near Greyed-Purple 187B.

The rachis is average in size, grooved on its upper side, with some stipitate glands on the edges. The under side is sparsely prickly, with stipitate glands.

The stipules are medium-length to long; moderately narrow and with medium-length to long points turning out at an angle of less than 45°.

The plant displays a more than average resistance to mildew and blackspot when compared to other commercialized varieties grown under comparable conditions in Ontario, Calif.

GROWTH

The plant exhibits a bushy, upright-spreading habit and considerable branching. The rose Macmigmou develops canes of from about 4 feet to 8 feet in length, with a median length of about 6 feet. The canes are self-supporting but have a tendency to weep or arch with the blossom weight; however, in doing so, they do not reach the ground. Its growth is very vigorous, with canes which are medium to heavy caliper.

The main stems are near Yellow Green 147D in color. They bear several large prickles of medium-length and which are almost straight; the base is of medium-length, moderately narrow and near Greyed-Green 197D in color. There are a few small prickles near Greyed-Green 197D in color and no hairs.

The branches are between Yellow-Green 146B and Green 137A in color. They bear several large prickles which are of medium-length, almost straight and have a medium length, moderately narrow base. These large prickles are near Greyed Orange 177B in color. There are a few small prickles of near Greyed-Orange 177B in color and no hairs.

New shoots exhibit a coloration between Yellow-Green 147A and 139A suffused with near Greyed-Purple 187B, in color. They bear several to many large prickles which are medium-length, almost straight and with a medium length narrow base. The color of these large prickles is near Greyed Purple 187C. There are several small prickles near Greyed-Purple 187C in color and no hairs.

I claim:

1. A new and distinct variety of rose plant of the hybrid shrub class, substantially as herein shown and described, and being especially characterized by its orange and white blooms with a distinct near white "eye" coloration in the center of each flower; the abundance of its "eyed" flowers borne on pyramidal clusters; a vigorous easily grown shrub with excellent disease resistance; and its total dropping of faded petalage.

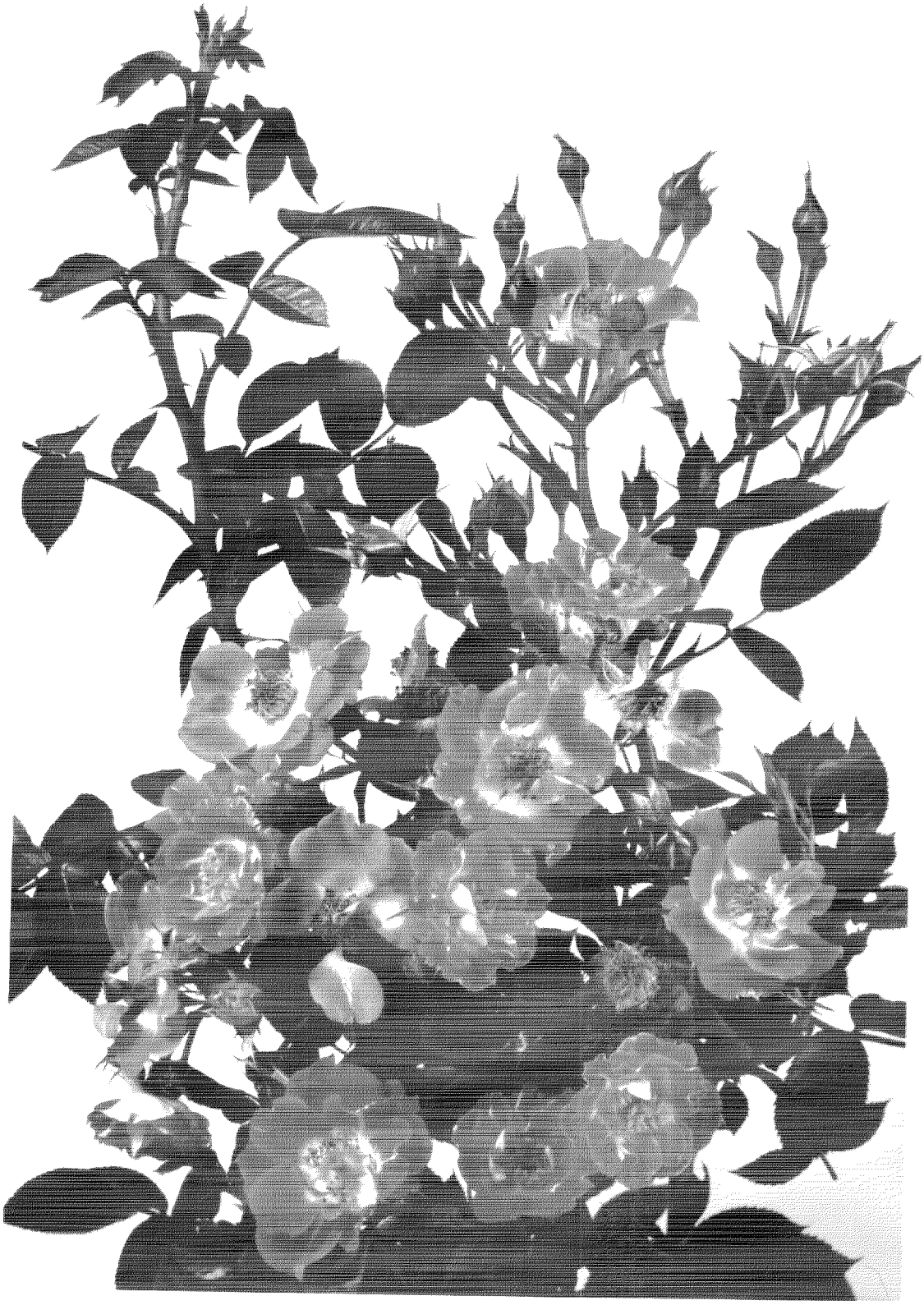

* * * * *